United States Patent

Wirch et al.

[11] Patent Number: 5,881,716
[45] Date of Patent: Mar. 16, 1999

[54] DEVICE FOR DOSING OF LIQUID

[75] Inventors: Alfred Wirch, Tann; Joachim Kretschmer, Rüti, both of Switzerland

[73] Assignee: Pelikan Produktions AG, Zurich, Switzerland

[21] Appl. No.: 717,247

[22] Filed: Sep. 20, 1996

[30] Foreign Application Priority Data

Sep. 21, 1995 [DE] Germany ............... 195 35 010.3

[51] Int. Cl.$^6$ ............................................. A61M 11/00
[52] U.S. Cl. ................... 128/200.16; 128/200.14; 128/200.21
[58] Field of Search ............... 128/200.14, 200.21, 128/200.16; 239/102.1, 102.2

[56] References Cited

U.S. PATENT DOCUMENTS 5,492,611 2/1996 Sugama et al. .................. 204/415

FOREIGN PATENT DOCUMENTS 55-94660A 7/1980 Japan.

*Primary Examiner*—Mickey Yu
*Assistant Examiner*—Dinh X. Nguyen
*Attorney, Agent, or Firm*—Fay, Sharpe, Beall, Fagan, Minnich & McKee

[57] ABSTRACT

The device has a current supply (1) connected to a control unit (2) including operating keys (3). The operating keys (3) provide for the inputting of a selectable dose amount or dosage per time unit or dose period. A liquid reservoir (5) stores fluid to be expelled. A droplet generator (8) includes a plurality of jets (13) connected to piezo-electrical or thermo-electrical converters which generate heat. Each jet and associated converter is individually controlled by the control unit. The device provides exact dosing of extremely small amounts of liquid, for example in the medicinal field, specifically with respect to inhalators or infusion instruments.

3 Claims, 3 Drawing Sheets

DEVICE FOR DOSING OF LIQUID

BACKGROUND OF THE INVENTION

The present invention relates to the medical arts. It finds particular application in conjunction with a device for controlling the amount and rate of an administered dose of liquid. However, it is to be appreciated that the present invention will also find application in conjunction with other systems requiring delivery of selected amounts of a fluid.

It frequently happens in medical technology that additional doses of small amounts of liquids need to be added, for example in an inhalator to the flow of oxygen, over a certain period of time or in a specified dosage to the infusion solution of an infusion apparatus. Similar problems occur also in other areas of technology when relatively small amounts of liquids need to be added or applied.

According to the invention, the solution is taking advantage of the technology which was developed for ink jet printers. An ink jet print head has a multitude of jets (for example 12–300), which are connected with an ink reservoir. Each jet is assigned a thermo-electrical or piezo-electrical converter. The converters are individually controlled by the printer and expel a volume of ink from the respective jet during actuation.

It was possible to ascertain through tests that when a great many droplets are expelled, the droplet mass, on average, remains almost constant. Therefore, this principle is suitable also for dosing of medicaments.

SUMMARY OF THE INVENTION

In accordance with one aspect of the present invention, a device for administering a dose of fluid is provided. A liquid reservoir stores the fluid and is in fluid communication with at least one jet which expels droplets of the fluid. A droplet generator which generates predetermined droplets is connected to the at least one jet and causes the droplets to be expelled through the at least one jet. A control unit selectively controls the droplet generator to generate the predetermined droplets and a current supply unit supplies the electrical power to the control unit.

One advantage of the present invention is that a dose amount or dosage frequency is selectable by an operator. The present invention provides exact dosing of even extremely small amounts of fluid to be delivered to inhalators, infusion instruments, or the like.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENT

Figure 1:
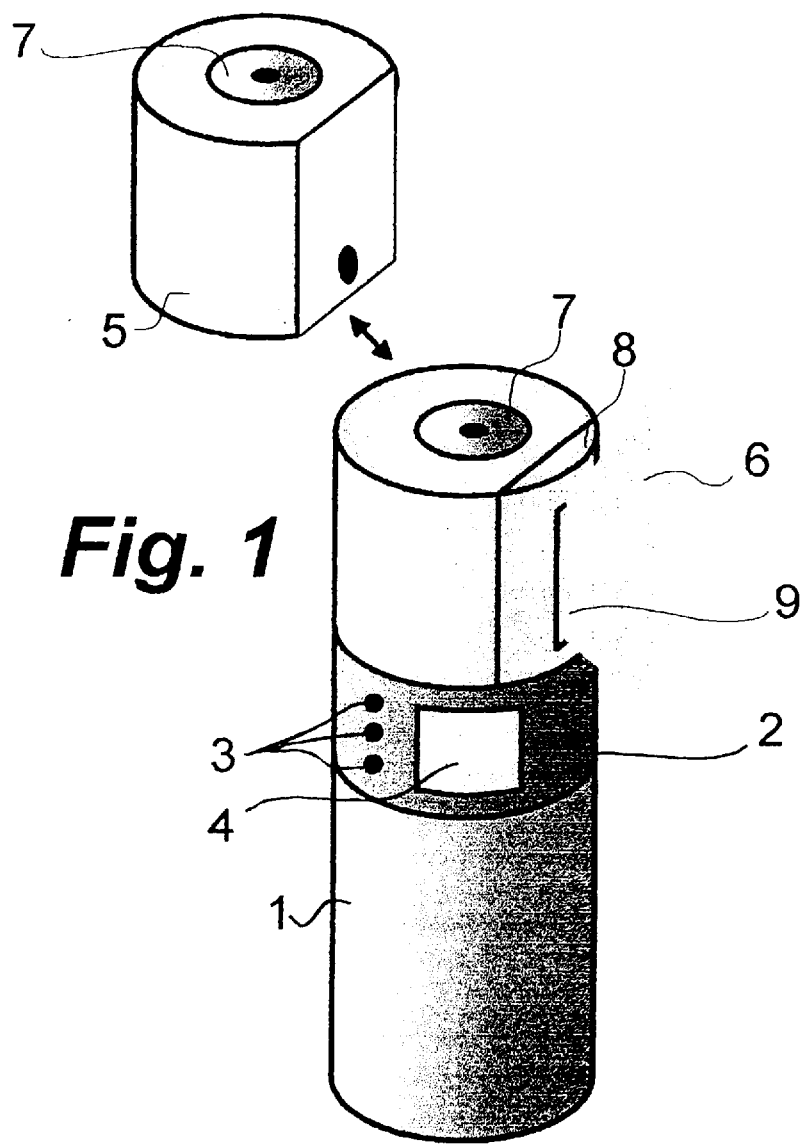
FIG. 1 is a device for atomization of a liquid, specifically for an inhalator.

A preferred embodiment of the invention is sketched in FIG. 1. This involves an instrument for atomization of liquids in the medical field. In case of illness of the respiratory tracts, it is necessary to finely diffuse medicaments, i.e., to generate droplets of very small volume and low velocity, in order to deliver them, though inhalation, to the respective locations where the effect is desired.

The device according to FIG. 1 has an energy supply 1 which includes, for example, a battery, an accumulator, solar cells or a current supply. In the event that an accumulator is the energy supply, a charging display may be included. The device has a control unit 2 which drives a droplet generator 8, facilitates turning the device on an off, and provides for the input of an operating time or to select different operating modes, such as amount of dosage. Operation of the controller 2 can, for example, be done in the form of control instruments such as buttons 3 in connection with a display 4. Other operating possibilities, however, are also conceivable, for example, a remote control. A liquid reservoir 5 contains a liquid 6 that is to be atomized. The liquid 6 can include a single component liquid or mixtures. It is also possible to diffuse minute particles, so-called pigments, which are contained in a liquid matrix.

The liquid reservoir 5 is preferably designed as an exchangeable or replaceable container, so that when the liquid volume is depleted, it can be replenished in a simple manner. Alternatively, the liquid reservoir can be constructed to be refillable such as by a refill hole. In both instances, it is appropriate after replenishment of the liquid volume to perform a rinsing process of the lines containing the liquid in order to guaranty safe operation of the device after the container is replaced. This can be accomplished by a pump 7 which is located in the reservoir 5 or in the device. Preferably, a filling level monitor is used to control the level of the liquid. Thus, the filling level can be displayed or the depletion of the liquid in the reservoir can be directly observed.

Figure 2:
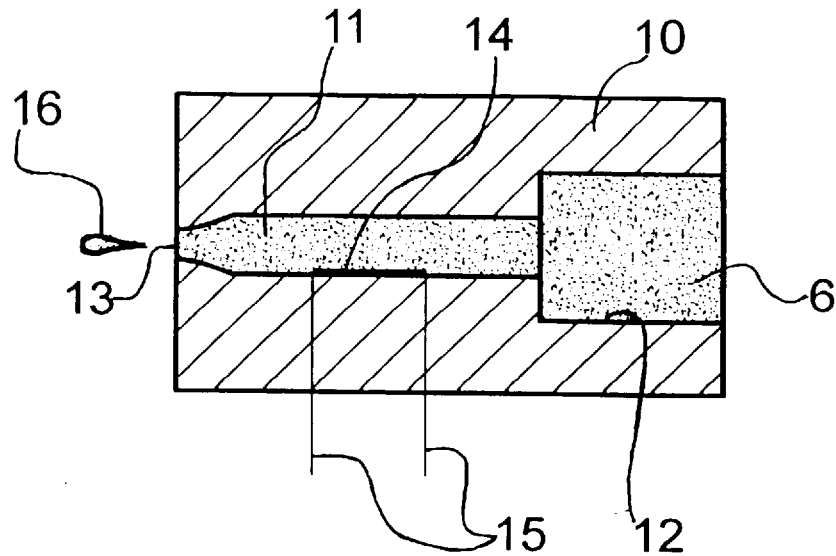
FIG. 2 shows one embodiment of a droplet generator in accordance with the present invention.
Figure 3:
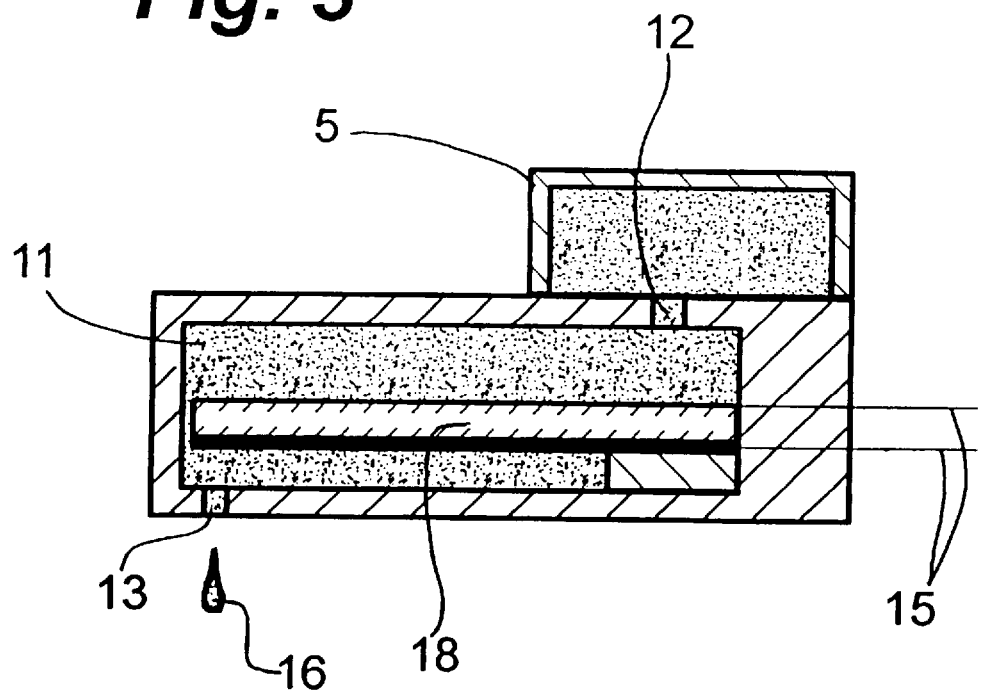
FIG. 3 shows another embodiment of the droplet generator in accordance with the present invention.

With referenced to FIGS. 2 and 3, examples of droplet generator 8 are shown. One embodiment according to FIG. 2 has, in a housing 10, a plurality of narrow ducts 11 which all lead into a supply duct 12 for the liquid 6 that is to be atomized. The duct 12 is connected with reservoir 5. Duct 11 carries the liquid to a liquid expelling jet 13. Preferably, the device includes a plurality of jets 13, each connected to the liquid reservoir via a duct. An electrical heating element and converter 14 is mounted to operate with each of the jets 13. The converter 14 is connected to lines 15. When a current impulse is applied to the lines 15, heat is generated which causes a small amount of liquid to evaporate in an explosion-like fashion so that a liquid volume 16 is expelled from the jet 13. After that, through capillary effect, the duct 11 is again filled with liquid 6. The heating elements 14, the protective layers and the conductor paths 15 are manufactured by thin film substrate technology, preferably on silicon as known by those of ordinary skill in the art.

In another embodiment shown in FIG. 3, the narrow ducts 11 lead into a chamber 17 filled with the fluid 6. Above each jet 13 of the ducts 11 in chamber 17, a piezo-electrical bending converter 18 is included which is controlled via the lines 15. By applying voltage impulses to the lines 15, the converter 18 bends back and forth which causes a liquid volume 16 to be expelled from jet 13.

The converters 14 and 18 are preferably controlled via a continuous, uniform chain of impulses, controlled according to a selected predetermined time interval, programmed via a keyboard or input keys 3, or determined by a desired number of drops to be ejected. By selecting an impulse form and impulse frequency, the liquid volume can be varied within relative wide boundaries.

With ink jet print heads, depending upon the type, droplets are generated ranging in size between 30 and 300 ng (nanogram). The maximum impulse frequency is approximately 10 kHz. With higher frequencies and/or other impulse forms, however, significantly smaller droplet sizes can be generated, ranging between 1–10 ng, preferably about 4 ng. This droplet size is ideally suited for inhalators. As a result of inhaling the fluid vapor, additional fluid circulation results.

Figure 4:
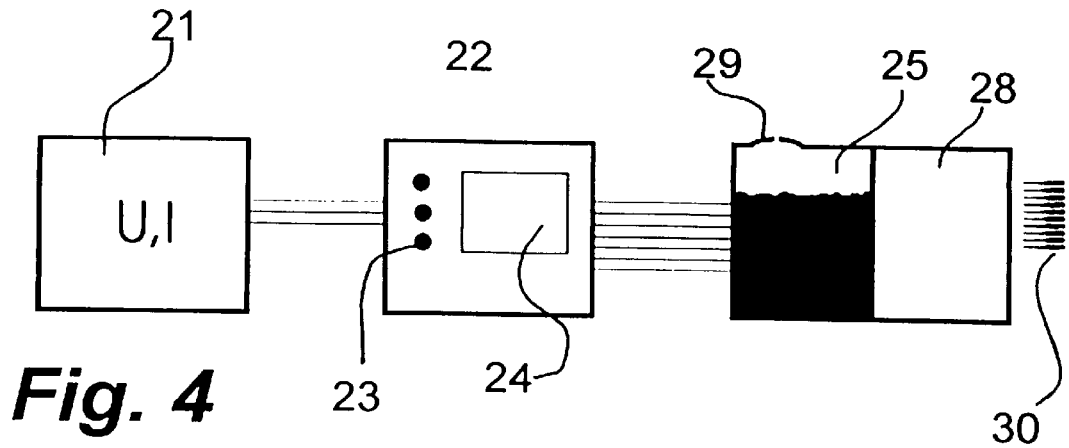
FIG. 4 shows one application of the present invention.
Figure 5:
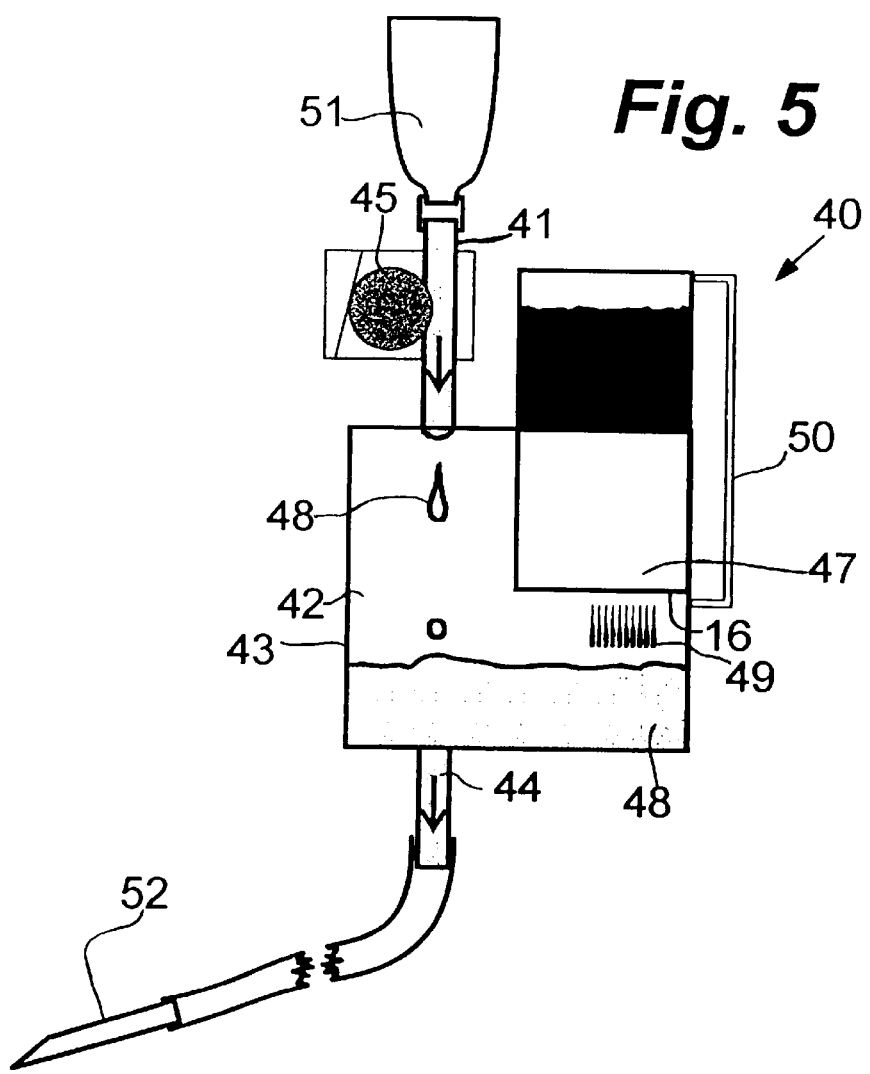
FIG. 5 shows another application of the present invention.

With reference to FIG. 4, another embodiment of the invention includes an apparatus which controls the precise dosage of small amounts of liquid. It substantially contains the same components as the embodiment shown in FIG. 1. It comprises an energy supply part 21, a control unit 22 with operating elements 23 and 24, a liquid reservoir 25 which contains the liquid that is to be metered out, and a droplet generator 28. Here again, the liquid reservoir is, ideally, exchangeable or replaceable in order to guaranty simple refilling of the device. To that end, a pumping device 29 is included in order to purge any air occluded during the replacement of liquid from the lines carrying the liquid out of the droplet generator. This ensures safe operation. In this particular application, the individual components are constructed separately, inasmuch as there is no need for compact design.

The jets 13 and the operating mode of the converters, i.e., the applied impulse form is selected in such a manner that a highly constant droplet size is created, such as for example 100 ng. Programming of the control unit 22, via input 23 is performed to produce a desired dosage or dosage per time unit. From these values, the control unit ascertains the required droplet size or the droplets per time unit. From this, the number and selection of converters 14 or 18 to be activated is determined, as well as the impulse frequency and, if necessary, the length of the impulse sequence or the impulse number. The impulse frequency may amount to in excess of 10 kHz. If the droplet generator 28 for example, contains 300 jets 13, each with an associated converter 14 or 18, the device can deliver a liquid amount ranging between 100 nanograms and several dozen milligrams of liquid per second. As a result, precise dosing of small amounts of liquid is achieved.

In FIG. 5, such an instrument 40 is employed for dosing of medications in infusions. In the connection line 41 and 44 between an infusion bottle 51 and a catheter 52 there is a drip unit 42. The drip unit 42 prevents air from getting into the catheter 52 and thereby into the blood stream. It also permits visual display of the flow of the infusion liquid. The drip unit 42 comprises a hose 41, which is hermetically connected with a transparent tube 43 having a larger cross-section than the hose 41. A second hose 44 is connected to the tube 43 and establishes the connection between drip unit 42 and catheter 52. The flow of liquid to the catheter 52 is determined, on the one hand, by the difference in height between catheter 52 and drip unit 42, and, on the other hand, by the negative pressure which occurs in the drip unit vessel. The negative pressure in the drip unit 42 is, in turn, dependent upon the post-dripping infusion liquid, which, in turn, depends upon the differences in height and the available flow cross-sections. For this reason, an adjustable throttle 45 is located in the supply line to regulate the flow.

The drip unit 42 is positioned in a suitable location for connection to the dosing instrument 40. There must be assurance that the jet front side 46 of the droplet generator 47 will not be moistened by the infusion fluid 48 so that safe droplet ejection 49 can take place. To prevent the dosing fluid from being sucked out of the droplet generator 47 due to the commencing negative pressure in the drip unit 42, a pressure compensation is provided via the connection 50 between the drip unit chamber and the dosing liquid reservoir.

Dosing of an additive is performed in a continuous manner by setting a desired droplet frequency for a given number of jets. Dosing of an additive can be accomplished intermittently by setting a predetermined time period such that a selected number of droplets is expelled. With the device of this type, dosing extremely small amounts of liquid is possible. Through aimed droplet ejection, it is also possible to topically accurately place an exact amount of liquid. However, for the above described application, this is not required.

In an alternate application, the present invention can be used for delivering lubricating agents in selected doses to a selected system, such as for lubrication of roller bearings. The accurate placement of minute amounts of lubricating fluid by the present invention optimizes the amount of spent lubricating agents. This requirement can also be satisfied by means of device 40.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the preferred embodiment, the invention is now claimed to be:

1. A device for selectively administrating a dose of fluid including a liquid medicament, comprising:

a liquid reservoir for storing the fluid;

a plurality of jets for expelling droplets of the fluid into an inhalator;

means for generating predetermined droplets from the fluid stored in the liquid reservoir and expelling the droplets from the plurality of jets in a selected fluid amount and a selected frequency, the means for generating the droplets including one of a thermo-electrical and piezo-electrical converter, and including one converter connected to each of the plurality of jets for individually controlling fluid expellsion from each of the plurality of jets;

a control unit for selectively controlling the generating means to generate the predetermined droplets; and a current supply unit electrically connected to the control unit for supplying electrical power.

2. The device according to claim 1, wherein the liquid reservoir is attachable and detachable to the means for generating droplets.

3. The device according to claim 1 wherein the control unit generates a frequency and impulse form for controlling each of the converters to generate droplets having a size between 1–10 nanograms.

* * * * *